US012544505B2

(12) United States Patent
Arnold et al.

(10) Patent No.: US 12,544,505 B2
(45) Date of Patent: Feb. 10, 2026

(54) SKIN-MOUNTABLE MEDICAL DEVICE

(71) Applicant: Roche Diabetes Care, Inc., Indianapolis, IN (US)

(72) Inventors: Marc Arnold, Hesse (DE); Christian Freitag, Weinolsheim (DE); Mads Bjoern Rasmussen, Weinheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 868 days.

(21) Appl. No.: 17/351,700

(22) Filed: Jun. 18, 2021

(65) Prior Publication Data

US 2021/0308370 A1 Oct. 7, 2021

Related U.S. Application Data

(63) Continuation of application No. PCT/EP2019/085524, filed on Dec. 17, 2019.

(30) Foreign Application Priority Data

Dec. 21, 2018 (EP) .................................... 18215163

(51) Int. Cl.
*A61M 5/142* (2006.01)

(52) U.S. Cl.
CPC ... *A61M 5/14248* (2013.01); *A61M 2209/088* (2013.01)

(58) Field of Classification Search
CPC ............ A61M 5/14248; A61M 5/1723; A61M 5/14244; A61M 5/1413; A61M 2209/088; A61B 5/145; A61B 5/6833; A45C 11/002; A45F 5/1516
See application file for complete search history.

(56) References Cited

U.S. PATENT DOCUMENTS

| | | | | |
|---|---|---|---|---|
| 6,302,866 | B1 | 10/2001 | Marggi | |
| 9,248,232 | B2 * | 2/2016 | Yodfat | A61B 5/14532 |
| 2009/0076453 | A1 | 3/2009 | Mejlhede et al. | |
| 2011/0213340 | A1 | 9/2011 | Howell et al. | |

(Continued)

FOREIGN PATENT DOCUMENTS

| | | |
|---|---|---|
| JP | 2011-507555 | 3/2011 |
| JP | 2011-520507 A | 7/2011 |

(Continued)

OTHER PUBLICATIONS

International Search Report and Written Opinion of the International Searching Authority, PCT/EP2019/085524, Feb. 18, 2020, 9 pages.

*Primary Examiner* — Bhisma Mehta
*Assistant Examiner* — Haden Matthew Ritchie
(74) *Attorney, Agent, or Firm* — Bose McKinney & Evans LLP

(57) ABSTRACT

A skin-mountable medical device having a mounting plate having a bottom side attachable to the skin of a user and a medical module, in particular, an analyte sensing device or a drug administration pump. A snap connector releasably attaches the medical module on the upper side of the mounting plate. The snap connector has a release flap that can be actuated by the user to detach the medical module, and the release flap projects outwardly from the mounting plate and at its bottom side maintains a clearance to avoid an interfering skin contact in use.

24 Claims, 2 Drawing Sheets

(56) References Cited

U.S. PATENT DOCUMENTS

| | | | |
|---|---|---|---|
| 2012/0078170 A1 | 3/2012 | Smith et al. | |
| 2012/0277667 A1 | 11/2012 | Yodfat et al. | |
| 2013/0085449 A1 | 4/2013 | Saulenas et al. | |
| 2017/0224912 A1 | 8/2017 | Yodfat et al. | |
| 2020/0343924 A1* | 10/2020 | Jackson ............... | F16M 11/041 |

FOREIGN PATENT DOCUMENTS

| | | | |
|---|---|---|---|
| JP | 2013-537844 | A | 10/2013 |
| JP | 2014-128710 | | 7/2014 |
| RU | 2 419 460 | C2 | 5/2011 |
| RU | 2 609 290 | C2 | 2/2017 |
| WO | WO 2008/078318 | A2 | 7/2008 |
| WO | WO 2009/001346 | A1 | 12/2008 |
| WO | WO 2009/125398 | A2 | 10/2009 |
| WO | WO 2009/139857 | A1 | 11/2009 |
| WO | WO 2012/040528 | A1 | 3/2012 |
| WO | WO 2016/189066 | A1 | 12/2016 |

* cited by examiner

SKIN-MOUNTABLE MEDICAL DEVICE

RELATED APPLICATIONS

This application is a continuation of PCT/EP2019/085524, filed Dec. 17, 2019, which claims priority to EP 18 215 163.9, filed Dec. 21, 2018, the entire disclosures of both of which are hereby incorporated herein by reference.

BACKGROUND

This disclosure relates to a skin-mountable medical device comprising a mounting plate having a bottom side attachable to the skin of a user preferably via an adhesive pad, a medical module, in particular an analyte sensing device or a drug administration pump, and a snap connector adapted to releasably attach the medical module on the upper side of the mounting plate opposite to the bottom side.

Such medical device is known from WO 2009/125398 A2. There, the device comprises a skin-adherable cradle unit and a fluid dispensing unit, wherein the cradle unit has two latches and the dispensing unit is snap-fitted by operation of the latches 32, 34. For this purpose, the latches are configured as hook-like protrusions which are accommodated in complementary shaped grooves of the dispensing unit. However, WO 2009/125398 A2 fails to disclose details for user handling of the latches, and the latches appear susceptible to breakage upon insertion of the dispensing unit. Such breaking connections may lead to a loss of the medical device, which may even go unnoticed by the patient.

SUMMARY

This disclosure further improves the known medical devices and to provide an easy-to-use design which simplifies user manipulation while avoiding assembly failures.

The combination of features stated in the independent claim is proposed to achieve this object. Advantageous embodiments and further developments of this disclosure are derived from the dependent claims.

This disclosure is based on the idea of improving user interaction by avoiding interfering contours or contact in the mechanical movement paths. Accordingly, it is proposed that wherein the snap connector has a release flap that can be actuated or pushed by the user to detach the medical module, wherein the release flap projects outwardly from the mounting plate and has an outer portion which at its bottom side maintains a clearance to avoid an interfering skin contact when used or pressed. In this way, the release flap is allowed to move prior to a skin contact, and the user is prevented from applying excessive forces against a skin abutment which may lead to material failure. Moreover, the effort and force for insertion of the medical module is reduced, as no movable part of the snap connector comes into skin contact, thus also avoiding a bending or deformation of the mounting plate. As a result, the user-device-interaction is improved, and the intended medical success is further supported.

Advantageously, where the bottom side of the mounting plate lies in a plane or is generally planar, the outer portion of the release flap should be arranged at a clearance distance of at least 2 mm, preferably at least 5 mm above this plane. In this way, there is provided sufficient tolerance for unimpeded movement of the flap.

In another advantageous configuration, where the release flap has an inner portion connected to the mounting plate, the distance of the inner portion to a plane which is defined by the bottom side of the mounting plate (or, in use, by the skin) should be smaller than the distance of the outer portion to said plane.

In this connection it is further advantageous when the bottom sides of the mounting plate and of the release flap each define a plane, and wherein said planes include an acute angle.

Preferably, said acute angle is at least 5°, preferably at least 10°.

In another advantageous embodiment, the bottom side of the release flap runs parallel to the bottom side of the mounting plate. In such a parallel configuration, the release flap may be directly attached to an upstanding part of a latch of the snap connector.

A particular advantageous embodiment further comprises that the release flap has an upstanding circumferential rim which in use faces away from the skin. Thereby, the user receives a haptic feedback when pressing his finger against the flap. Furthermore, the rim facing upwards avoids unintended slipping of the finger and thereby supports higher pressing forces.

In an advantageous embodiment, the snap connector has a latch that is connected to the mounting plate and engages with the medical module in a locking position, wherein the latch can be tilted outward by actuation of the release flap so as to disengage from the medical module in a release position.

For providing a mechanically secure connection, the latch has a hook portion which is adapted to snap into a recess of the medical module.

In order to support the application of the medical module onto the mounting plate, the snap connector has an inlet chamfer which is construed to guide the medical module into a locking position, wherein the inlet chamfer is arranged at an acute angle with respect to the bottom side of the mounting plate.

Another possibility for facilitating handling and improving joining provides that a securing bracket is provided for attaching the medical module, wherein the securing bracket and the snap connector are arranged at opposite ends of the mounting plate.

In still another advantageous configuration, the mounting plate and the release flap are formed as an integral, preferably injection-molded plastic part.

The medical device according to any of claims 1 to 12, in an advantageous configuration for drug administration, a fitting can be arranged on the bottom plate to provide a skin access preferably for a cannula assembly of the medical module.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
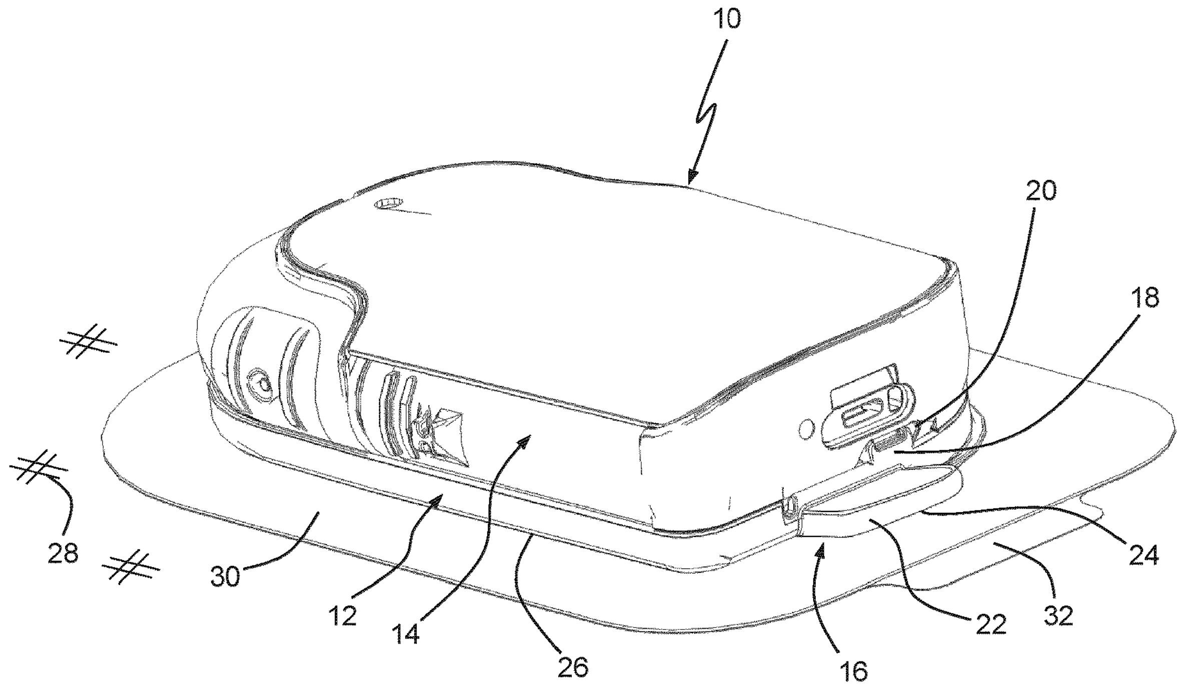
FIG. 1 is a perspective view of a body-wearable medical device including a mounting base with an improved release mechanism.

Referring to FIG. 1, a medical device 10 has a mounting base or plate 12, a medical module 14 in the form of a body-worn patch pump for administration of insulin and a release mechanism formed as a snap connector 16 which is adapted to releasably attach the medical module 14 on the mounting plate 12, e.g., for first time assembly or removal in case of temporarily non-use or replacement. For this purpose, the snap connector 16 comprises a latch 18 that engages with a recess or notch 20 in a sidewall of the medical module 14 and a release tap or flap 22 that can be pushed down by the user or patient into a bottom free space or clearance 24 such that the flap 22 is allowed to move prior to a skin contact.

The mounting plate 12 has a bottom side 26 which is attachable at an infusion site to the skin 28 of the user via a self-adhesive pad 30 which is protected on its adhesive side by a peel-off foil 32.

Figure 2:
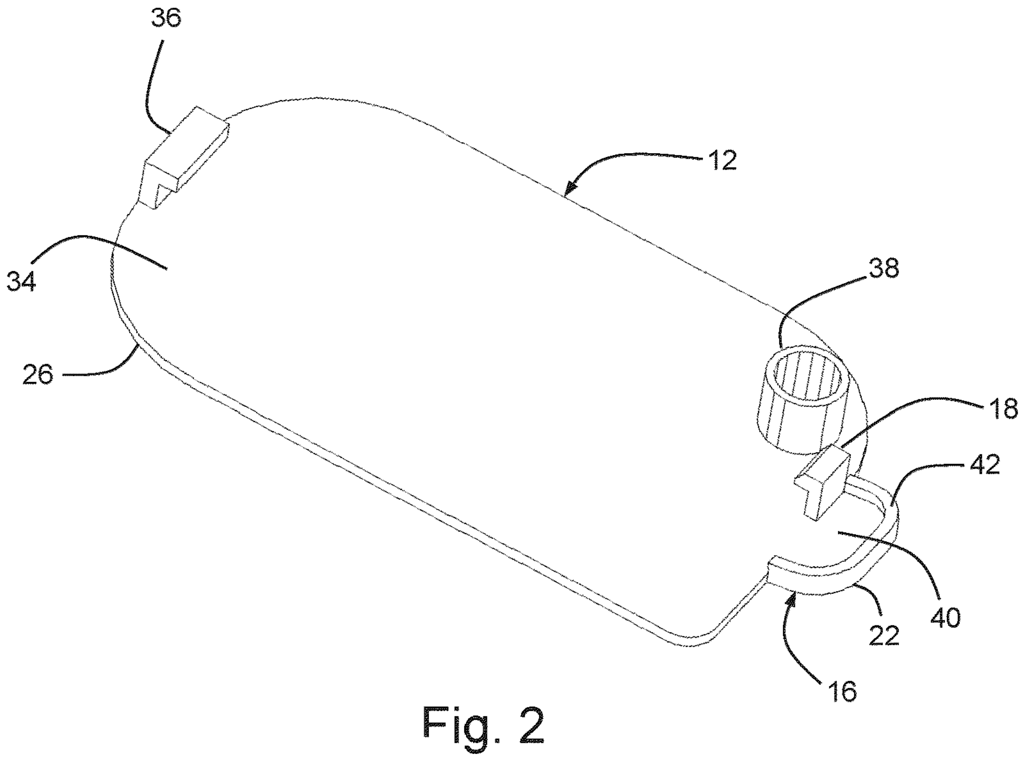
FIG. 2 is a perspective view of the mounting base of the medical device of FIG. 1.

As can be seen best in FIG. 2, the mounting plate 12 has a top or upper side 34 which in use faces away from the skin 28 and supports the medical module 14. The latch 18 and a securing hook or bracket 36 are provided at opposite ends of the oblong mounting plate 12 as upstanding elements on the upper side 34. An upstanding hollow fitting or socket 38 provides skin access for a cannula assembly (not shown).

At the joining area of the latch 18, the flap 22 is molded onto the edge of the mounting plate 12, such that it projects outwardly and is tilted upwards away from the skin 28, as will be explained in more detail below. Advantageously, the flap 22 has a flat base portion 40 and an upstanding circumferential rim 42 on the free outer edge of the base portion facing away from the skin 28.

The mounting plate 12 including its attached elements, 18, 22, 36, 38 may be formed as an integral one-piece plastic part, e.g., by injection-molding.

Figure 3:
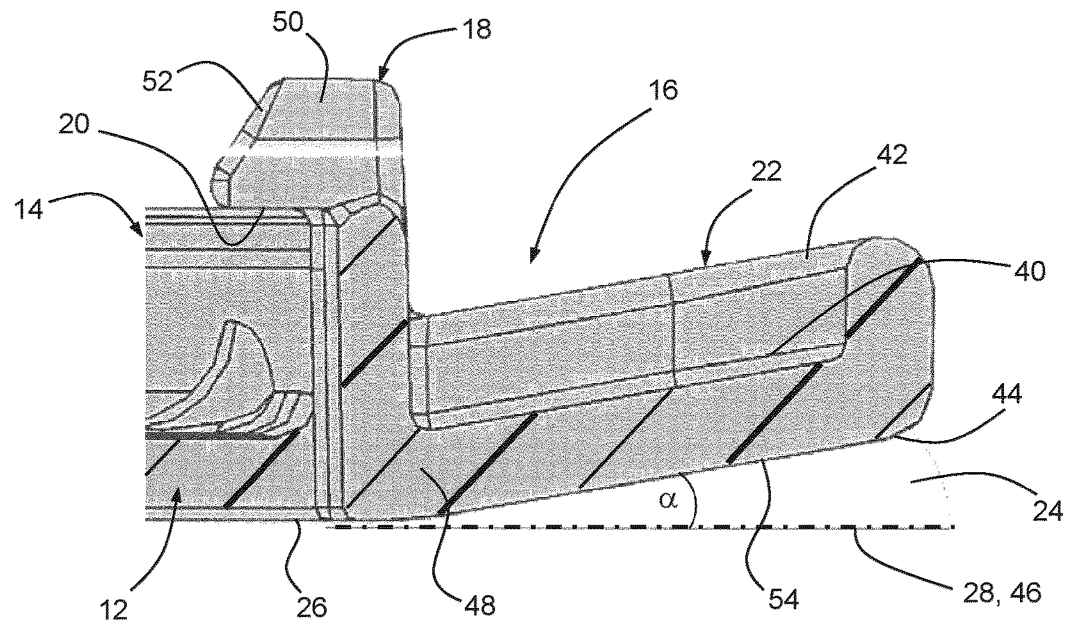
FIG. 3 is an enlarged view of the release mechanism of the medical device.

As further illustrated in FIG. 3, the outer portion 44 of the release flap 22 maintains at its bottom side clearance 24, such that the release flap 22 is allowed to move under a force implied by finger pressure without interference, thus avoiding contact to the skin 28 or the self-adhesive pad 30 arranged thereupon. Then, the outer clearance distance to a plane 46 defined by the skin 28 (or, coinciding therewith, defined by the flat bottom side 26 of the mounting plate 12) should be about 5 mm, when viewed in direction perpendicular to the plane 46.

FIG. 3 further illustrates that the latch 18 has a hook portion 50 which is adapted to snap into the recess 20 of the medical module 14. The hook portion 50 is provided with an inlet chamfer 52 which guides the medical module 14 when introduced into the shown locking position. For this purpose, the inlet chamfer 52 is arranged at an acute angle with respect to the bottom side 26 of the mounting plate 12. For removal of the medical module 14, the latch 18 can be tilted outward (to the right in FIG. 3) by actuation of the release flap 22 so as to disengage from the recess 20 in a release position.

In the embodiment of FIG. 3, in order to allow a movement prior to an interfering skin contact, the distance of the connecting portion 48 of the flap 22 to the plane 46 should be smaller than the distance of the outer portion 44 to said plane 46. This can be realized arranging the flat bottom side 54 of the flap 22 under an acute angle $\alpha$ with respect to the skin 28 or plane 46. Preferably, said angle $\alpha$ is above 5°, e.g., around 10°.

Figure 4:
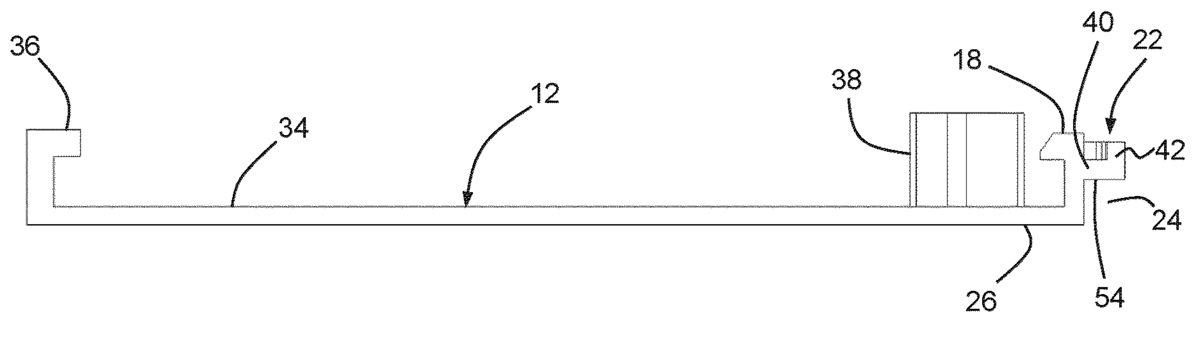
FIG. 4 is a side view of the mounting base with a further embodiment of the release mechanism.

In the embodiment of FIG. 4, similar parts are indicated with similar reference signs as explained above. The main difference is in the arrangement of the release flap 22, which in this case on its bottom side runs at a distance parallel to the bottom side 26 of the mounting plate 12, thus maintain a free space with a constant clearance 24. In this configuration, the release flap 22 may be directly attached to the upstanding section of the latch 18.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A skin-mountable medical device, comprising:

a mounting plate having a bottom side attachable to the skin of a user wherein the bottom side of the mounting plate lies in a plane;

a medical module comprising an analyte sensing device or a drug administration pump;

a snap connector adapted to engage and releasably attach the medical module on an upper side of the mounting plate opposite the bottom side; and a release flap configured to be depressed to release the medical module from the snap connector wherein the release flap projects in a direction away from the snap connector and the periphery of the mounting plate and has an outer portion having a bottom side that maintains a clearance from the plane of the bottom side of the mounting plate when the release flap is depressed to release the medical module from the snap connector.

2. The medical device according to claim 1, the outer portion of the release flap is arranged at a clearance distance of at least 2 mm.

3. The medical device according to claim 2, wherein the outer portion of the release flap is arranged at a clearance distance of at least 5 mm.

4. The medical device according to claim 1, wherein the release flap has an inner portion connected to the mounting plate, and the distance from the inner portion to the plane defined by the bottom side of the mounting plate is smaller than the distance of the outer portion to said plane.

5. The medical device according to claim 1, wherein the bottom side of the release flap defines a second plane, and wherein the second plane is tilted upwardly and defines an acute angle ($\alpha$) with the plane defined by the bottom side of the mounting plate.

6. The medical device according to claim 5, wherein said acute angle ($\alpha$) is at least 5°.

7. The medical device according to claim 6, wherein said acute angle ($\alpha$) is at least 10°.

8. The medical device according to claim 1, wherein the bottom side of the release flap runs substantially parallel to the bottom side of the mounting plate whereby the bottom side of the release flap defines a constant clearance.

9. The medical device according to claim 1, wherein the release flap has an upstanding circumferential rim which in use is configured to project away from the skin.

10. The medical device according to claim 1, wherein the snap connector has a latch connected to the mounting plate which engages with the medical module in a locking position, and wherein the latch is configured to be outwardly tilted by actuation of the release flap to thereby disengage from the medical module in a release position.

11. The medical device according to claim 10, wherein the latch has a hook adapted to snap into a recess of the medical module.

12. The medical device of claim 11, wherein the latch includes an upstanding part projecting from the mounting plate and the release flap extends from the upstanding part of the latch, wherein the bottom side of the release flap runs substantially parallel to the bottom side of the mounting plate whereby the bottom side of the release flap defines a constant clearance, and wherein the release flap has an upstanding circumferential rim disposed thereon which in use is configured to project from the flap and away from the skin.

13. The medical device according to claim 1, wherein the snap connector has an inlet chamfer configured to guide the medical module into a locking position, wherein the inlet chamfer is arranged at an acute angle with respect to the bottom side of the mounting plate.

14. The medical device according to claim 1, further comprising a securing bracket configured for attaching the medical module, wherein the securing bracket and the snap connector are arranged at opposite ends of the mounting plate.

15. The medical device according to claim 1, wherein the mounting plate and the release flap are integrally formed.

16. The medical device according to claim 1, further comprising a fitting arranged on the bottom plate to provide a skin access for a cannula assembly of the medical module.

17. The medical device according to claim 1, wherein the snap connector has an arm that extends upwardly from the mounting plate and the release flap projects away from the mounting plate in a direction substantially parallel to the mounting plate.

18. The medical device according to claim 1, further comprising a self-adhesive pad disposed on the bottom side of the mounting plate and wherein the release flap is moveable without contact with the self-adhesive pad.

19. The medical device according to claim 1, wherein the release flap extends from the edge of the mounting plate proximate where the snap connector extends from the upper side of the mounting plate.

20. A skin-mountable medical device, comprising:

a mounting plate having a bottom side attachable to the skin of a user wherein the bottom side of the mounting plate lies in a plane;

a medical module comprising an analyte sensing device or a drug administration pump;

a snap connector adapted to engage and releasably attach the medical module on an upper side of the mounting plate opposite the bottom side; and a release flap pivotable downwardly toward the skin of the user to release the medical module from the snap connector wherein the release flap projects in a direction away from the snap connector and the mounting plate and has an outer portion that maintains a clearance from the plane of the bottom side of the mounting plate when the outer portion of the release flap is pivoted downwardly toward the skin of the user to release the medical module from the snap connector.

21. The medical device of claim 20, wherein the snap connector has an arm that extends upwardly in a direction away from the upper side of the mounting plate.

22. The medical device according to claim 21, wherein the release flap extends from the edge of the mounting plate proximate where the snap connector extends from the upper side of the mounting plate and wherein the release flap has an upstanding circumferential rim disposed thereon which in use is configured to project from the flap and away from the skin.

23. The medical device of claim 20, wherein the downward pivoting of the release flap is in a direction substantially orthogonal to the direction of movement of the snap connector caused thereby.

24. The medical device according to claim 20, further comprising a self-adhesive pad disposed on the bottom side of the mounting plate and wherein the release flap is moveable without contact with the self-adhesive pad.

* * * * *